United States Patent [19]

Mori et al.

[11] Patent Number: 5,698,199
[45] Date of Patent: Dec. 16, 1997

[54] LIPOLYSIS ACCELERATION METHOD

[75] Inventors: Shinobu Mori; Yuji Ichii; Norihiro Tanaka; Hidenori Yorozu; Satoshi Kanazawa; Yoshinori Nishizawa, all of Ichikai-machi, Japan

[73] Assignee: Kao Corporation, Tokyo, Japan

[21] Appl. No.: 612,018

[22] Filed: Mar. 5, 1996

[30] Foreign Application Priority Data

Mar. 10, 1995 [JP] Japan .................. 7-050881
May 10, 1995 [JP] Japan .................. 7-111549

[51] Int. Cl.$^6$ .................................. A61K 35/78
[52] U.S. Cl. ............ 424/195.1; 514/844; 514/909
[58] Field of Search .............. 424/195.1; 514/909, 514/844

[56] References Cited

FOREIGN PATENT DOCUMENTS 3 190809  8/1991  Japan .
6 206814  7/1994  Japan .

*Primary Examiner*—John W. Rollins
*Attorney, Agent, or Firm*—Oblon, Spivak, McClelland, Maier & Neustadt, P.C.

[57] ABSTRACT

The present invention provides a lipolysis acceleration method which comprises orally administering a thistle-series or pepper-family plant, or an extract thereof; or dermatologically applying it by local administration or as a bath medicine composition. According to the method of the present invention, marked lipolysis acceleration effects can be obtained. It exhibits excellent effects for the control, prevention and improvement of obesity.

10 Claims, No Drawings

LIPOLYSIS ACCELERATION METHOD

BACKGROUND OF THE INVENTION

1. Field of the Invention

This invention relates to a lipolysis acceleration method, and more specifically to a lipolysis acceleration method useful for the control and prevention of obesity, the improvement of endomorphic constitution, and the reduction of a local or systemic adipose tissue.

2. Description of the Related Art

Obesity is caused by accumulation of excessive intake energies than the body can consume on white fat cells as neutral fat. It has been pointed out that obesity accompanied with substantial splanchnic fat accumulation is associated with a morbid condition such as insulin resistance or arteriosclerosis. On the other hand, obesity involving significant subcutaneous fat accumulation is a serious problem from the viewpoint of aesthetic sense irrespective of sex.

Habitual drinking of oolong tea or Chinese gutta percha tea has heretofore been considered to be desired for the control, prevention and improvement of obesity. With a view to controlling the calorie intake, it has also been the practice to eat sparingly or to use low-energy foods, an appetite controller, an intestinal suppressor or the like.

These methods however are accompanied with the problems that the habitual drinking of oolong tea or Chinese gutta percha tea and the control of a calorie intake are not always fully effective for the improvement, that they can hardly be accepted as a habit, and that they cannot accelerate the decomposition of accumulated fat. These methods are therefore not thorough solutions.

Accordingly, an object of the present invention is to provide a lipolysis acceleration method which can accelerate decomposition of an accumulated adipose tissue to achieve sufficient control, prevention and improvement of obesity.

With the foregoing in view, the present inventors have carried out an extensive investigation. As a result, it has been found that a thistle-series or pepper-family plant or an extract thereof, which has heretofore been never considered to have any physiological action on adipose cells, can accelerate decomposition of neutral fat accumulated in an adipose tissue by its oral administration or dermatologic application, thereby permitting control, prevention and improvement of obesity, leading to the completion of the invention.

SUMMARY OF THE INVENTION

In one aspect of this invention, there is thus provided a lipolysis acceleration method, which comprises orally administering or dermatologically applying a thistle-series or pepper-family plant or an extract thereof.

In a further aspect of this invention, there is also provided a dermatologic medicine composition comprising (a) a thistle-series or pepper-family plant or an extract thereof and (b) a dermatologic medicine ingredient.

In a still further aspect of this invention, there is also provided a bath medicine composition comprising (a) a thistle-series or pepper-family plant or an extract thereof and (b) a bath medicine ingredient.

DETAILED DESCRIPTION OF THE PREFERRED EMBODIMENTS

Examples of the thistle series plant for use in the present invention include those belonging to the genus Cephalonoplos such as *Cephalonoplos segetum* (Bieb.) Kitam. and *Cephalonoplos setosum* (Bieb.) Kitam.; those belonging to the genus Cirsium such as *Cirsium purpuratum* (Maxim.) Matsum., *Cirsium pendulum* Fischer, *Cirsium ugoense* Nakai, *Cirsium grayanum* (Maxim.) Nakai, *Cirsium kamtschaticum* Ledeb., *Cirsium sieboldii* Miq., *Cirsium lucens* Kitam., *Cirsium yezoense* (Maxim.) Makino, *Cirsium tenuisquamatum* Kitam., *Cirsium tashiroi* Kitam., *Cirsium hidaense* Kitam., *Cirsium spinosum* Kitam., *Cirsium maritimum* Makino, *Cirsium brevicaule* A. Gray, *Cirsium boninense* Koidz., *Cirsium japonicum* DC., *Cirsium japonicum* DC. var australe Kitam., *Cirsium joponicum* DC. var takaoense Kitam., *Cirsium oligophyllum* (Franch. et Savat.) Matsum., *Cirsium chokaiense* Kitam., *Cirsium borealinipponense* Kitam., *Cirsium okamotoi* Kitam., *Cirsium maruyamanum* Kitam., *Cirsium diabolicum* Kitam., *Cirsium magofukui* Kitam., *Cirsium lineare* (Thunb.) Sch Bip., *Cirsium dipsacolepis* (Maxim.) Matsum., *Cirsium kagomontanum* Nakai, *Cirsium suzukii* Kitam., *Cirsium gyojanum* Kitam., *Cirsium confertissimum* Nakai, *Cirsium bitchuense* Nakai, *Cirsium aidzuense* Nakai, *Cirsium buevgeri* Miq., *Cirsium longepedunculatum* Kitam., *Cirsium heiianum* Koidz., *Cirsium suzukaense* Kitam., *Cirsium furusei* Kitam., *Cirsium effusum* (Maxim.) Matsum., *Cirsium congestissimum* Kitam., *Cirsium spicatum* (Maxim.) Matsum., *Cirsium tenue* Kitam., *Cirsium microspicatum* Nakai, *Cirsium inundatum* Makino, *Cirsium norikurense* Nakai, *Cirsium amplexifolium* Kitam., *Cirsium matsumurae* Nakai, *Cirsium ganjuense* Kitam., *Cirsium babanum* Koidz. var otayae (Kitam.), *Cirsium suffultum* (Maxim.) Matsum., *Cirsium nipponicum* (Maxim.) Makino, *Cirsium yakushimense* Masam., *Cirsium chikushiense* Koidz., and *Cirsium hanamakiense* Kitam.; those belonging to the genus Carduns such as *Carduns cripus* L.; those belonging to the genus Saussurea such as *Saussurea pulcheila* Fischer, *Saussurea japonica* (Thunb.) DC., *Saussurea chionophylla* Takeda, *Saussurea nikoensis* Franch et Savat., *Saussurea brachycephala* Franch., *Saussurea franchetii* Koidz., *Saussurea yanagisawae* Takeda, *Saussurea fauriei* Franch., *Saussurea gracilis* Maxim., and *Saussurea scaposa* Franch et Savat.; those belonging to the genus Hemistepta such as *Hemistepta lyrata* Bunge; those belonging to the genus Synurus such as *Synurus excelsus* (Makino) Kitam., *Synurus palmatopinnatifidus* (Makino) Kitam. var indivisus Kitam., and *Synurus pungens* (Franch et Savat.) Kitam.; those belonging to the genus Serratula such as *Serratula coronata* L. Subsp. insularis (Iljin) Kitam.; those belonging to the genus Atractylodes such as *Atractylodes japonica* Koidz. ex Kitam.; and those belonging to the genus Echinops such as *Echinops setifer* Iljin. Of these, preferred are those belonging to the genera Cephalonoplos, Cirsium and Carduns, with *Cephalonoplos segetnum* (Bieb.) Kitam., *Cephalonoplos setosum* (Bieb.) Kitam., *Cirsium borealinipponense* Kitam., *Cirsium spicatum* (Maxim.) Matsum., *Cirsium japonicum* DC., *Cirsium oligophyllum* (Franch. et Savat.) Matsum., *Cirsium maritimum* Makino, *Cirsium japonicum* DC. var australe Kitam. and *Carduns cripus* L. being particularly preferred.

Of these thistle series plants, *Cephalonoplos segetnum* (Bieb.) Kitam., *Cirsium japonicum* DC. and the like have hemostatic, antiphlogic and diuretic effects and are known as crude drugs (for example, Japanese Patent Laid-Open No. 190809/1991), but their lipolysis acceleration effects in fat tissues are not known at all.

With respect to the thistle series plant in the present invention usable as a raw material, are not only its leaves, head flowers, seeds, stems and roots but also the entire plant. Among these, use of roots and stems is particularly preferred.

Examples of the pepper family plants for use in the present invention include *Piper nigrum* L., *Piper longum* L., *Peperomia japonica* Makino, *Peperomia buninsimensis* Makino, *Peperomia caperata* Ruiz. et Pav., *Peperomia incana* A. Dietr, *Peperomia magnolifolia* A. Dietr. var variegata R. et P., *Peperomia puteolata* Trel., *Peperomia sandersii* C. DC. var. argyreia Bailey, *Piper betele* L., *Piper cubeba* L., *Piper methysticum* Forst, *Piper retrofractum* Vahl, *Piper aurantiacum* Wall. var hupehense C. DC., *Piper kadzura* Ohwi, *Piper boehmeriaefolium* Wall, *Piper hainanense* Hemsl, *Piper haucei* Maxim., and *Piper sarmentosum* Roxb. Of these, *Piper higrum* L. and *Piper longum* L. are particularly preferred.

In the present invention, mature or immature fruits, pericarps, seeds, leaves, petioles, branches, roots, flowers and the like can be used as a raw material. Among them, fruits, pericarps and leaves are preferred.

Of the above-described pepper family plants, *Piper nigrum* L. has been widely used as a condiment and is known to have perspiration and stomachic effects (for example, Japanese Patent Laid-Open No. 206814/1994). Edible peppers are so-called black pepper obtained by drying immature fruits and so-called white pepper obtained by removing epicarps from mature fruits and then drying the insides. For the objects of the present invention, use of green peppers obtained either from raw fruits or from immature green fruits to which a drying or freezing treatment has been beforehand made to prevent their blackning is preferred.

In the present invention, the thistle-series or pepper-family plant can be used as is or in the form of squeezed juice, dried powder, a solvent extract or the like, with the use in the form of a solvent extract being particularly preferred.

Examples of the solvent extract include extracts with water, organic solvents such as lower alcohols and polyols, and mixed solvents thereof. Such solvent extracts can be used after subjecting them to concentration, purification, sterilization, drying or the like as desired. Particularly preferred is an extract with water, ethanol or a water-ethanol mixture. As an extraction method with such a solvent, particularly preferred is to conduct the extraction at −5° to 100° C. for 30 to 48 minutes with the solvent in an amount 1 to 100 times as much as the weight of the thistle-series or pepper-family plant or the dried powder thereof. The extract so obtained can be used as is or converted into a powder form by lyophilization, spray drying or the like.

In the present invention, the thistle-series or pepper-family plant or the extract thereof, which may hereinafter be collectively called the "ingredient (a), may be administered orally or applied dermatologically, with the dermatologic application being preferred. Examples of the dermatologic application include application of a composition, in which the ingredient (a) is contained, to the skin and bathing in bathwater to which a composition with the ingredient (a) contained therein has been added.

In the present invention, it is possible to incorporate, in addition to the ingredient (a), one or more compounds selected from xanthine derivatives, β-adrenergic agents, α$_2$-adrenergic blockers and pyridine derivatives. Examples of the xanthine derivatives include xanthine, aminophylline, theophylline, choline-theophylline, caffeine, theobromine, oxytriphylline, diprophilline, proxyphylline and the like.

Illustrative examples of the β-adrenergic agents include isoproterenol, epinephrine, norepinephrine, dobutamine, dopamine, butopamine, salbutamol, terbutaline, isoetharine, protokylol, fenoterol, metaproterenol, chloroprenaline, hexoprenaline, trimetoquinol, procaterol hydrochloride, prenalterol, folskolin, disodium (R,R)-5-[2-[[2-(3-chlorophenyl)-2-hydroxyethyl]-amino]propyl]-1,3-benzodioxole-2,2-dicarboxylate, (R*,R*)-4-[2-({2-[(3-chlorphenyl)-2-hydroxyethyl]amino}propyl)phenyl] phenoxyacetic acid, {2-hydroxy-5-[2-({2-hydroxy-3-[4-(1-methyl-4-trifluoromethyl)-1H-imidazol-2-yl] phenoxy}propyl)amino]ethoxy}-benzamidomonomethanesulfonate and erythro-DL-1-(7-methylindan-4-yloxy)-3-isopropylaminobutan-2-ol, and pharmacologically-acceptable salts thereof.

Examples of the α$_2$-adrenergic blockers include yohimbine, phentolamine, phenoxybenzamine, tolazoline, ergotamine, ergotoxine, dihydroergotamine, ergometrine, methyl ergometrine, dihydroergotoxine, lauwolscine and piperoxan, and pharmacologically acceptable salts thereof.

Examples of the bipyridine derivatives include amrinone, milurinone, 5-cyano-[3,4'-bipyridin]-6(1H)-one and 5-carbamyl-[3,4'-bipyridin]-6(1H)-one, and pharmacologically acceptable salts thereof.

Upon oral administration of the ingredient (a) in the present invention, the ingredient (a) can be formulated into tablets, capsules, liquids, powders, granules or the like by adding a pharmaceutically-acceptable carrier. In the case of oral administration, it is desired to administer the ingredient (a) at a daily dose of from 0.01 to 5 g, particularly from 1 to 2 g per adult as measured in the form of a dried solvent extract.

Upon dermatologic application of the ingredient (a) in the present invention, it is preferred to use the ingredient (a) in the form of a dermatologic medicine composition containing it in combination with a dermatologic medicine ingredient (b). Examples of the dermatologic medicine ingredient (b) include surfactants, oily ingredients, moisturizing agents, high-molecular compounds, ultraviolet absorbers, anti-inflammatory agents, sterilizers, antioxidants, sequestering agents, antiseptics, vitamins, coloring agents, perfumes and the like, all of which are used in various preparations such as pharmaceuticals and cosmetics.

Although anionic, cationic, nonionic, natural and synthetic surfactants can all be used, use of a non-ionic one is preferred in consideration of skin irritation.

Examples of the nonionic surfactant include glycerin fatty acid esters, propylene glycol fatty acid esters, sorbitan fatty acid esters, polyoxyethylene sorbitan fatty acid esters, polyoxyethylene sorbitol fatty acid esters, polyoxyethylene alkyl ethers, polyoxyethylene polyoxypropylene glycols, polyoxyethylene polyoxypropylene alkyl ethers, polyethylene glycol fatty acid esters, polyoxyethylene castor oils, polyoxyethylene hydrogenated castor oils, alkyl glycosides and the like.

Illustrative of the oil ingredients include fats and fatty oils, waxes, hydrocarbons, higher fatty acids, higher alcohols, esters, essential oils, and silicone oils. Examples of the fats and fatty oils include natural ones such as soybean oil, rice oil, jojoba oil, avocado oil, almond oil, olive oil, cacao oil, sesame oil, persic oil, castor oil, coconut oil, mink oil, tallow and lard; hydrogenated oils obtained by the hydrogenation of these natural fats and fatty oils and synthetic triglycerides such as myristic glyceride and 2-ethylhexanoic acid triglyceride. Examples of the waxes include carnauba wax, spermaceti wax, yellow bees wax and lanolin. Illustrative examples of hydrocarbons include liquid paraffin, vaseline, paraffin microcrystalline wax, ceresin, squalane and pristane. Examples of the higher fatty acids include lauric acid, myristic acid, palmitic acid, stearic acid, behenic acid, oleic acid, linoleic acid, linolenic acid, lanolic acid and isostearic acid. Exemplary higher alcohols include lauryl alcohol, cetyl alcohol, stearyl alcohol, oleyl alcohol, lanolin alcohol, cholesterol and 2-hexyldecanol. Examples of the esters include cetyl octanoate, triglyceride octanoate, myristyl lactate, cetyl lactate, isopropyl myristate, myristyl myristate, octyl dodecyl myristate, isopropyl palmitate, isopropyl adipate, butyl stearate, decyl oleate, cholesteryl isostearate and POE sorbitol fatty acid esters. Illustrative examples of the essential oils include menta oil, jasmine oil, camphor oil, cypress oil, spruce oil, pomegranate oil, turpentine oil, cinnamon oil, bergamot oil, mandarin oil, calamus oil, pine oil, lavender oil, bay oil, clove oil, hiba oil, rose oil, eucalyptus oil, lemon oil, thyme oil, peppermint oil, sage oil, menthol, ceneole, eugenol, citral, citronellal, borneol, linalool, geraniol, camphor, thymol, spilanthole, pinene, limonene and terpene compounds. Examples of the silicone oils include dimethyl polysiloxane. The above-exemplified oily ingredients can be used either singly or in combination. Of these, it is particularly preferred to use myristic glyceride, 2-ethylhexanoic acid triglyceride, lanolin, liquid paraffin, vaselin, paraffin microcrystalline wax, squalane, lauric acid, myristic acid, palmitic acid, linoleic acid, linolenic acid, isostearic acid, cetyl alcohol, stearyl alcohol, oleyl alcohol, cholesterol, cetyl octanoate, triglyceride octanoate, isopropyl myristate, octyl dodecyl myristate, cholesteryl isostearate, POE sorbitol fatty acid esters, menta oil, spruce oil, cinnamon oil, rose oil, menthol, cineole, eugenol, citral, citronellal, geraniol, pinene, limonene and dimethyl polysiloxane.

Examples of the coloring agents include the dyes in the Annexed Lists I and II of Synthetic Organic Food Additives prescribed under the Ministry of Health and Welfare Act, such as Yellow Color No. 4, Blue Color No. 1 and Yellow Color No. 202; and natural coloring matters approved as food additives, such as chlorophyll, riboflavin, crocin, safflower and anthraquinone. Illustrative examples of the vitamins include vitamins A, C, D and E.

The dermatologic medicine composition according to the present invention can be prepared in a manner known per se in the art. Examples of their preparation forms include cream, milky liquid, jelly, paste, poultice, plaster and the like. To the dermatologic medicine composition of the present invention, it is preferred to add the ingredient (a) in an amount of at least 0.005 wt. % (hereinafter referred to simply as "%"), particularly from 0.01 to 30% as measured in the form of its dried solvent extract.

For the dermatologic application of the ingredient (a) by adding it to bathwater in the present invention, it is preferred to use it in combination with a bath medicine ingredient (c) as a bath medicine composition. Examples of the bath medicine ingredient (c) include inorganic salts, organic acids, carbonates, oily ingredients, dispersing or emulsifying agents, inorganic acids, crude drugs, coloring agents, vitamins, perfumes and the like.

Examples of the inorganic salts include sodium chloride, sodium bicarbonate, sodium carbonate, borax, sodium sulfate, sodium sulfide, sodium sesquicarbonate, sodium nitrate, sodium thiosulfate, sodium polyphosphate, sodium phosphate, calcium oxide, magnesium oxide, calcium carbonate, magnesium carbonate, potassium chloride and potassium sulfide. Of these, sodium chloride, sodium bicarbonate, sodium carbonate, sodium sulfate, sodium sesquicarbonate, magnesium oxide, calcium carbonate and magnesium carbonate are preferred. It is desired to add the inorganic salt in an amount of 5% or more, particularly 10% or more, based on the total weight of the bath medicine composition.

In the bath medicine composition according to the present invention, combined use of the ingredient (a) with an organic acid and a carbonate makes one feel warmer for an extended period of time after bathing.

Examples of the organic acid useful in the present invention include succinic acid, fumaric acid, malic acid, tartaric acid, citric acid, benzoic acid and the like. They can be used either singly or in combination.

Illustrative examples of the carbonate useful in the present invention include sodium bicarbonate, sodium carbonate, potassium bicarbonate, calcium carbonate, magnesium carbonate, sodium sesquicarbonate and the like. They can be used either singly or in combination. In the present invention, it is preferred to use sodium bicarbonate, sodium carbonate, sodium sesquicarbonate or magnesium carbonate as a carbonate and succinic acid or fumaric acid as an organic acid.

It is desired to add the carbonate in an amount of from 5 to 80%, particularly from 10 to 50%, based on the total weight of the composition; and to add the organic acid in an amount of from 10 to 300%, particularly from 30 to 150% based on the carbonate.

When an organic acid and a carbonate are used in combination in the bath medicine composition of the present invention, it is preferred to add an acidic ingredient as needed for making bathwater weakly-acidic (preferably pH 5 to 7) so that $CO_2$ given off in the bathwater can be dissolved therein and blood circulation accelerating effects can be obtained owing to $CO_2$ so dissolved. Although no particular limitation is imposed on such an acidic ingredient, it is preferred to add the above-described organic acid in an excess amount.

In the bath medicine composition according to the present invention, use of an oily ingredient in combination with the ingredient (a) makes it possible to enhance moisturized feeling to the skin. As the oily ingredient, those exemplified above as ingredients for the dermatologic medicine composition can also be referred to. Although the content of the oily ingredient in the bath medicine composition can be selected freely depending on the preparation type (form) of the bath medicine, it can generally fall within a range of from 0.1 to 95% based on the total composition.

To the bath medicine composition according to the present invention, a dispersing or emulsifying agent for the oily ingredient can be added as needed.

The dispersing or emulsifying agent serves to prevent the oily ingredient of the bath medicine composition from coming up to the water surface when the composition is added to the bathwater. In addition, it makes the bathwater turbid. Described specifically, when the bathwater contains the agent in an amount of 0.01%, the clearness of the bathwater is reduced to 40 cm or lower, preferably 20 cm or lower. The dispersing or emulsifying agent can thus give a high-class image to the bath such as a milky bath.

Examples of such a dispersing or emulsifying agent include water-soluble high-molecular compounds and surfactants. Specific examples of the water-soluble high-molecular compounds include sodium alginate, propylene glycol alginate, gum arabic, xanthane gum, pectin, tragacanth, sodium carboxymethylcellulose, methyl cellulose, carboxyvinyl polymers, polyethylene glycol, polyvinyl alcohols, polyvinyl pyrrolidones, milk protein, soybean protein, gelatin, egg protein, caseinate, whey protein and the like. Of these, gum materials such as gum arabic and xanthane gum and water-soluble proteins such as sodium caseinate and whey protein are preferred.

Although anionic, cationic, nonionic, natural and synthetic surfactants can all be used, use of a non-ionic surfactant is preferred in consideration of skin irritation.

Examples of the nonionic surfactant include glycerin fatty acid esters, propylene glycol fatty acid esters, sorbitan fatty acid esters, polyoxyethylene sorbitan fatty acid esters, tetraoleic acid polyoxyethylene sorbitol, polyoxyethylene alkyl ethers, polyoxyethylene polyoxypropylene glycol, polyoxyethylene polyoxypropylene alkyl ethers, polyethylene glycol fatty acid esters, polyoxyethylene castor oils, polyoxyethylene hydrogenated castor oils and polyglycerine fatty acid esters.

These dispersing or emulsifying agents can be used either singly or in combination. It is preferred to add the dispersing or emulsifying agent in an amount of from 5 to 100% based on the oily ingredient.

Examples of the inorganic acid include boric acid, metasilicic acid and silicic anhydride.

Illustrative examples of the crude drug include fennel, german chamomile, ginkgo, phellodendron bark, cinammon bark, safflower, peony root, ginger, sweet-flag, cnidium rhizome, Japanese angelica root, citrus unshiu peel, atractylodes lancea rhizome, Japanese valerian, angelica dahurica root, bitter orange peel, mentha herb, hoelen and ginseng.

The bath medicine composition of the present invention can further contain sulfur, geyserite, mine sand, mica powder, neutral clay and/or parched rice-bran.

The bath medicine composition of the present invention can be produced in a manner known per se in the art. Exemplary preparation forms include powders, granules, tablets, liquids and the like.

It is preferred to use the bath medicine composition in such an amount that the concentration of the ingredient (a) as measured in the form of its dried solvent extract falls within a range of from 0.01 to 200 ppm, preferably from 0.1 to 100 ppm, more preferably from 0.5 to 50 ppm in the bathwater.

It is desired to use the dermatologic medicine composition and bath medicine composition of the present invention for the purpose of accelerating lipolysis in fat tissues. When used so, they exhibit excellent effects for the control, prevention and improvement of obesity.

EXAMPLES

The present invention will hereinafter be described more specifically by the following examples. It should however be borne in mind that this invention is by no means limited to or by the examples.

Invention products 1-6 and Comparative products 1-3 used in the examples are as follows:

Invention Product 1

In a manner known per se in the art, 100 g of dried roots of *Cephalonoplos segetum* (Bieb.) Kitam. were extracted with hot water. After filtration, the filtrate was concentrated under reduced pressure. The concentrate was then lyophilized, whereby a hot-water extract of Cephalonoplos was obtained as Invention Product 1.

Invention Product 2

In a manner known per se in the art, 100 g of dried stems of *Cephalonoplos sererum* (Bieb.) Kitam. were extracted with a 30% aqueous ethanol solution. After filtration, the filtrate was concentrated under reduced pressure. The concentrate was then lyophilized, whereby a 30%-ethanol extract of Cephalonoplos was obtained as Invention Product 2.

Invention Product 3

In a manner known per se in the art, 100 g of dried roots of *Cirsium japonicum* DC. were extracted with hot water. After filtration, the filtrate was concentrated under reduced pressure. The concentrate was then lyophilized, whereby a hot-water extract of *Cirsium japonicum* DC. was obtained as Invention Product 3.

Invention Product 4

In a manner known per se in the art, 100 g of dried green fruits of *Piper higrum* L. (green peppers) were extracted with hot water. After filtration, the filtrate was concentrated under reduced pressure. The concentrate was then lyophilized, whereby a hot-water extract of *Piper nigrum* L. was obtained as Invention Product 4.

Invention Product 5

In a manner known per se in the art, 100 g of dried green fruits of *Piper nigrum* L. (green peppers) were extracted with a 30% aqueous ethanol solution. After filtration, the filtrate was concentrated under reduced pressure. The concentrate was then lyophilized, whereby a 30%-ethanol extract of *Piper nigrum* L. was obtained as Invention Product 5.

Invention Product 6

In a manner known per se in the art, 100 g of dried fruits of *Piper longum* L. were extracted with hot water. After filtration, the filtrate was concentrated under reduced pressure. The concentrate was then lyophilized, whereby a hot-water extract of *Piper longum* L. was obtained as Invention Product 6.

Comparative Product 1

In a manner known per se in the art, 100 g of dried leaves of oolong tea were extracted with hot water. After filtration, the filtrate was concentrated under reduced pressure. The concentrate was then lyophilized, whereby a hot-water extract of oolong tea was obtained as Comparative Product 1.

Comparative Product 2

In a manner known per se in the art, 100 g of dried leaves of oolong tea were extracted with a 30% aqueous ethanol solution. After filtration, the filtrate was concentrated under reduced pressure. The concentrate was then lyophilized, whereby a 30%-ethanol extract of oolong tea was obtained as Comparative Product 2.

Comparative Product 3

In a manner known per se in the art, 100 g of dried leaves of Chinese gutta percha tea were extracted with hot water. After filtration, the filtrate was concentrated under reduced pressure. The concentrate was then lyophilized, whereby a hot-water extract of Chinese gutta percha tea was obtained as Comparative Product 3.

Example 1

Using Invention Products 1-3 and Comparative Products 1-3, their lipolysis acceleration effects were studied by the following testing method. The results are shown in Table 1.

(Testing method)

In accordance with the method reported by Rodbell, M. in J. Biol. Chem., 239, 375(1964), free fat cells were prepared from the epididymis tissues of five Wistar male rats (body weight: 150–200 g) using a collagenase solution. With respect to each of the Invention Products and Comparative Products, the product was added as test substance to Hank's buffer containing bovine serum albumin to give a test substance concentration of 100 µg/ml, whereby a culture medium was prepared. The above cells were incubated at 37° C. for 2 hours in the culture medium. Liberated glycerol was measured by an enzymatic method ("F-Kit Glycerol", trade name; product of Boeringer Manheim GmbH).

TABLE 1

| Test group | Liberated glycerol[1] |
| --- | --- |
| Buffer (Control) | 0.01 ± 0.01 |
| Invention Product 1 | 2.05 ± 0.22 |
| Invention Product 2 | 2.12 ± 0.31 |
| Invention Product 3 | 1.98 ± 0.20 |
| Comparative Product 1 | 0.02 ± 0.02 |
| Comparative Product 2 | 0.01 ± 0.02 |
| Comparative Product 3 | 0.01 ± 0.02 |

[1]Unit: μmol/ml. Expressed by mean ± SE (n = 5).

As is apparent from Table 1, when 100 μg/ml of the test substances were separately caused to act on the liberated fat cells, marked lipolysis acceleration effects were observed on Invention Products 1–3, while no such effects were observed on Comparative Products 1–3.

Example 2

Using Invention Products 4–6 and Comparative Products 1–3, their lipolysis acceleration effects were studied by the following testing method. The results are shown in Table 2.

(Testing method)

In accordance with the method reported by Rodbell, M. in J. Biol. Chem., 239, 375(1964), free fat cells were prepared from the epididymis tissues of five Wistar male rats (body weight: 150–200 g) using a collagenase solution. With respect to each of the Invention Products and Comparative Products, the product was added as test substance to Hank's buffer containing bovine serum albumin to give a test substance concentration of 100 μg/ml, whereby a culture medium was prepared. The above cells were incubated at 37° C. for 2 hours in the culture medium. Liberated fatty acid was measured by the method reported by Okuda, H. et al. in Pharmacol. Res. Commun., 18, 877(1986).

TABLE 2

| Test group | Liberated fatty acid[1] |
| --- | --- |
| Buffer (Control) | 0.1 ± 0.1 |
| Invention Product 4 | 11.2 ± 0.5 |
| Invention Product 5 | 12.8 ± 0.7 |
| Invention Product 6 | 6.0 ± 0.3 |
| Comparative Product 1 | 0.8 ± 0.1 |
| Comparative Product 2 | 0.3 ± 0.1 |
| Comparative Product 3 | 0.2 ± 0.1 |

[1]Unit: MEq/ml. Expressed by mean ± SE (n = 5).

As is apparent from Table 2, when 100 μg/ml of the test substances were separately caused to act on the liberated fat cells, marked lipolysis acceleration effects were observed on Invention Products 4–6, while no such effects were observed on Comparative Products 1–3.

Example 3

Dermatologic medical compositions of the compositions shown in Table 3 were prepared in a manner known per se in the art. Their lipolysis acceleration effects were studied by the following testing method. The results are shown in Table 3.

(Testing method)

From each of five male Wistar rats (body weight: 250–350 g), the abdominal skin tissue with the subcutaneous fat tissue attached thereon was peeled off in a size of 4 cm in diameter and was set on a cylindrical diffuser cell of 2.6 cm in diameter. Onto the surface of the skin, 0.5 g of one of the dermatologic medicine compositions shown in Table 3 was coated uniformly. The lower portion of the diffuser cell was filled with Hank's buffer. At 37° C., the skin coated with the composition was left over for three hours, followed by measurement of glycerol liberated in the buffer in the lower portion in accordance with an enzymatic method similar to that employed in Example 1.

TABLE 3

| Ingredient (%) | Invention Product | | | | | | Comparative Product | | | | |
| --- | --- | --- | --- | --- | --- | --- | --- | --- | --- | --- | --- |
| | 7 | 8 | 9 | 10 | 11 | 12 | 4 | 5 | 6 | 7 | 8 |
| Invention Product 1 (extract) | 10.0 | | 10.0 | 10.0 | 10.0 | 10.0 | | | | | |
| Invention Product 2 (extract) | | 15.0 | | | | | | | | | |
| Aminophylline | | | 0.5 | | | | | 0.5 | | | |
| Isoproterenol hydrochloride | | | | 0.5 | | | | | 0.5 | | |
| Yohimbine hydrochloride | | | | | 2.0 | | | | | 2.0 | |
| Amrinone | | | | | | 1.0 | | | | | 1.0 |
| Propylene glycol | 15.0 | 10.0 | 15.0 | 15.0 | 15.0 | 15.0 | 15.0 | 15.0 | 15.0 | 15.0 | 15.0 |
| Liquid paraffin | 9.0 | 9.0 | 9.0 | 9.0 | 9.0 | 9.0 | 19.9 | 19.0 | 19.0 | 19.0 | 19.0 |
| 2-Ethylhexanoic | 28.0 | 28.0 | 28.0 | 28.0 | 28.0 | 28.0 | 28.0 | 28.0 | 28.0 | 28.0 | 28.0 |

TABLE 3-continued

|  | Invention Product | | | | | | Comparative Product | | | | |
|---|---|---|---|---|---|---|---|---|---|---|---|
| Ingredient (%) | 7 | 8 | 9 | 10 | 11 | 12 | 4 | 5 | 6 | 7 | 8 |
| acid triglyceride | | | | | | | | | | | |
| Sorbitol | 8.0 | 8.0 | 8.0 | 8.0 | 8.0 | 8.0 | 8.0 | 8.0 | 8.0 | 8.0 | 8.0 |
| Polyethylene glycol [3] | 6.0 | 6.0 | 6.0 | 6.0 | 6.0 | 6.0 | 6.0 | 6.0 | 6.0 | 6.0 | 6.0 |
| Acyl methyl taurine | 6.0 | 6.0 | 6.0 | 6.0 | 6.0 | 6.0 | 6.0 | 6.0 | 6.0 | 6.0 | 6.0 |
| Polyoxyethylene (20) octyl dodecyl alcohol ether | 8.0 | 8.0 | 8.0 | 8.0 | 8.0 | 8.0 | 8.0 | 8.0 | 8.0 | 8.0 | 8.0 |
| Purified water | 10.0 | 10.0 | 9.5 | 9.5 | 8.0 | 9.0 | 10.0 | 9.5 | 9.5 | 8.0 | 9.0 |
| Perfume | trace | trace | trace | trace | trace | trace | trace | trace | trace | trace | trace |
| Free glycerol [2] | 4.3 ± 0.5 | 4.5 ± 0.4 | 6.0 ± 0.5 | 6.5 ± 0.8 | 6.1 ± 0.3 | 5.8 ± 0.3 | 1.5 ± 0.2 | 2.0 ± 0.3 | 2.8 ± 0.2 | 1.9 ± 0.4 | 2.0 ± 0.4 |

[2] Unit: $10^{-7}$ mol/ml. Expressed by mean ±SE (n = 5).
[3] Average molecular weight: 400.

As is apparent from Table 3, compared with Comparative Product 4 which was not added with any of the thistle-series plant extracts, Invention Products 7 and 8 were observed to have remarkable lipolysis acceleration effects on the panniculus adipose by the dermatologic application. It was also found that Invention Products 9 through 12, which were added with one of the thistle series plant extracts and the xanthine derivative, β-adrenergic agent, $\alpha_2$-adrenergic blocker or bipyridine derivative were enhanced in lipolysis acceleration effects compared with Comparative Products 5–8 which were not added with any of the thistle-series plant extracts.

Example 4

Dermatologic medicine compositions of the compositions shown in Table 4 were prepared in a manner known per se in the art. Their lipolysis acceleration effects were studied by the same testing method as that employed in Example 3. The results are shown in Table 4.

TABLE 4

|  | Invention Product | | | | | | Comparative Product | | | | |
|---|---|---|---|---|---|---|---|---|---|---|---|
| Ingredient (%) | 13 | 14 | 15 | 16 | 17 | 18 | 4 | 5 | 6 | 7 | 8 |
| Invention Product 4 (extract) | 15.0 | | 15.0 | 15.0 | 15.0 | 15.0 | | | | | |
| Invention Product 5 (extract) | | 15.0 | | | | | | | | | |
| Aminophylline | | | 0.5 | | | | | 0.5 | | | |
| Isoproterenol hydrochloride | | | | 0.5 | | | | | 0.5 | | |
| Yohimbine hydrochloride | | | | | 2.0 | | | | | 2.0 | |
| Amrinone | | | | | | 1.0 | | | | | 1.0 |
| Propylene glycol | 10.0 | 10.0 | 10.0 | 10.0 | 10.0 | 10.0 | 15.0 | 15.0 | 15.0 | 15.0 | 15.0 |
| Liquid paraffin | 9.0 | 9.0 | 9.0 | 9.0 | 9.0 | 9.0 | 19.0 | 19.0 | 19.0 | 19.0 | 19.0 |
| 2-Ethylhexanoic acid triglyceride | 28.0 | 28.0 | 28.0 | 28.0 | 28.0 | 28.0 | 28.0 | 28.0 | 28.0 | 28.0 | 28.0 |
| Sorbitol | 8.0 | 8.0 | 8.0 | 8.0 | 8.0 | 8.0 | 8.0 | 8.0 | 8.0 | 8.0 | 8.0 |
| Polyethylene glycol [3] | 6.0 | 6.0 | 6.0 | 6.0 | 6.0 | 6.0 | 6.0 | 6.0 | 6.0 | 6.0 | 6.0 |
| Acyl methyl taurine | 6.0 | 6.0 | 6.0 | 6.0 | 6.0 | 6.0 | 6.0 | 6.0 | 6.0 | 6.0 | 6.0 |
| Polyoxyethylene (20) octyl dodecyl alcohol ether | 8.0 | 8.0 | 8.0 | 8.0 | 8.0 | 8.0 | 8.0 | 8.0 | 8.0 | 8.0 | 8.0 |
| Purified water | 10.0 | 10.0 | 9.5 | 9.5 | 8.0 | 9.0 | 10.0 | 9.5 | 9.5 | 8.0 | 9.0 |
| Perfume | trace | trace | trace | trace | trace | trace | trace | trace | trace | trace | trace |
| Liberated glycerol [2] | 4.2 ± 0.5 | 4.4 ± 0.2 | 7.2 ± 0.3 | 7.5 ± 0.2 | 6.8 ± 0.4 | 6.9 ± 0.3 | 2.0 ± 0.3 | 2.8 ± 0.4 | 3.0 ± 0.3 | 2.3 ± 0.5 | 2.5 ± 0.2 |

[2] Unit: $10^{-7}$ mol/ml. Expressed by mean ±SE (n = 5).
[3] Average molecular weight: 400.

As is apparent from Table 4, compared with Comparative Product 4 which was not added with any of the pepper extracts, Invention Products 13 and 14 were observed to have remarkable lipolysis acceleration effects on the panniculas adipose by the dermatologic application. It was also found that Invention Products 15 through 18, which were added with one of the pepper family plant extracts and the xanthine derivative, β-adrenergic agent, $\alpha_2$-adrenergic blocker or bipyridine derivative were enhanced further in lipolysis acceleration effects compared with Comparative Products 5–8 which were not added with any of pepper-family plant extract.

Example 5

| Oral tablets | (%) |
|---|---|
| Powdered roots of *Cephalonoplos segetum* (Bieb.) Kitam. | 15 |
| Theophylline | 10 |
| Lactose | 30 |
| Dextrin | q.s. |
| Glucose | 15 |
| Coloring agent | trace |

Example 6

| Jelly cream | (%) |
|---|---|
| Invention Product 1 (extract) | 15 |
| Liquid paraffin | q.s. |
| Squalane | 20 |
| Microcrystalline wax | 5 |
| Cetyl isooctanoate | 5 |
| Polyoxyethylene (20) glycerol triisostearic acid ester | 1 |
| Perfume | trace |
| Coloring agent | trace |

Example 7

| Scrubber-containing massaging preparation | |
|---|---|
| Whole powder of *Cirsium japonicum* DC. | 10 |
| Isoproterenol hydrochoride | 1 |
| Polyethylene beads (Beads having a particle size of 20 μm or smaller: 7% and those having a particle size of 5000 μm or larger: 0%) | 10 |
| Liquid paraffin | 10 |
| 2-Ethylhexanoic acid triglyceride | 37 |
| Sorbitol | 8 |
| Polyethylene glycol (average molecular weight: 400) | 6 |
| Acyl methyl taurine | 6 |
| Polyoxyethylene (60) octyl dodecyl alcohol ether | 8 |
| Purified water | q.s. |
| Perfume | trace |

Example 8

| Foam pack | (%) |
|---|---|
| Invention Product 2 (extract) | 10 |
| Yohimbine hydrochloride | 2 |
| 1,3-Butylene glycol | 10 |
| Glycerin | 10 |
| Methyl paraben | 0.2 |
| Potassium hydroxide | 0.2 |
| Stearic acid | 1 |
| Butyl alcohol | 2 |
| Polyoxyethylene (60) hydrogenated castor oil | 3 |
| Liquefied petroleum gas (propellant) | 5 |
| Dimethyl ether (propellant) | 3 |
| Perfume | trace |
| Purified water | q.s. |

Example 9

| Tablet-type bath medicine | (%) |
|---|---|
| Invention Product 3 (extract) | 14 |
| Amrinone | 2 |
| Sodium bicarbonate | 20 |
| Sodium carbonate | 10 |
| Fumaric acid | 30 |
| Polyethylene glycol (average molecular weight: 6000) | 20 |
| Dextrin | q.s. |
| Perfume | trace |
| Coloring agent | trace |

Example 10

| Liquid bath medicine | (%) |
|---|---|
| Invention Product 3 (extract) | 20 |
| Octanoic acid triglyceride | 33 |
| Octyl dodecyl myristate | 33 |
| Liquid paraffin | q.s. |
| Polyoxyethylene sorbitol fatty acid ester (40E.O.) | 9 |
| Polyoxyethylene sorbitol fatty acid ester (20E.O.) | 3 |
| Perfume | trace |

Example 11

| Oral tablets | (%) |
|---|---|
| Green pepper powder | 20 |
| Theophylline | 10 |
| Lactose | 30 |
| Dextrin | q.s. |
| Glucose | 15 |
| Coloring agent | trace |

Example 12

| Jelly cream | (%) |
|---|---|
| Invention Product 4 (extract) | 10 |
| Liquid paraffin | q.s. |
| Squalane | 20 |
| Microcrystalline wax | 5 |
| Cetyl isooctanoate | 5 |
| Polyoxyethylene (20) glycerol triisostearate | 1 |
| Perfume | trace |
| Coloring agent | trace |

Example 13

| Scrubber-containing massaging preparation | |
|---|---|
| *Piper longum* L. fruit powder | 5 |
| Isoproterenol hydrochoride | 1 |
| Polyethylene beads (Beads having a particle size of 20 μm or smaller: 7% and those having a particle size of 5000 μm or larger: 0%) | 10 |
| Liquid paraffin | 14 |
| 2-Ethylhexanoic acid triglyceride | 37 |

Example 14

| Scrubber-containing massaging preparation | |
|---|---|
| Sorbitol | 8 |
| Polyethylene glycol (average molecular weight: 400) | 6 |
| Acyl methyl taurine | 6 |
| Polyoxyethylene (60) octyl dodecyl alcohol ether | 8 |
| Purified water | q.s. |
| Perfume | trace |

Example 14

| Foam pack | (%) |
|---|---|
| Invention Product 5 (extract) | 15 |
| Yohimbine hydrochloride | 2 |
| 1,3-Butylene glycol | 10 |
| Glycerin | 10 |
| Methyl paraben | 0.2 |
| Potassium hydroxide | 0.2 |
| Stearic acid | 1 |
| Butyl alcohol | 2 |
| Polyoxyethylene (60) hydrogenated castor oil | 3 |
| Liquefied petroleum gas (propellant) | 5 |
| Dimethyl ether (propellant) | 3 |
| Perfume | trace |
| Purified water | q.s. |

Example 15

| Tablet-type bath medicine | (%) |
|---|---|
| Invention Product 4 (extract) | 12 |
| Amrinone | 2 |
| Sodium bicarbonate | 20 |
| Sodium carbonate | 10 |
| Fumaric acid | 30 |
| Polyethylene glycol (average molecular weight: 6000) | 20 |
| Dextrin | q.s. |
| Perfume | trace |
| Coloring agent | trace |

Example 16

| Liquid bath medicine | (%) |
|---|---|
| Invention Product 5 (extract) | 10 |
| Octanoic acid triglyceride | 33 |
| Octyl dodecyl myristate | 33 |
| Liquid paraffin | q.s. |
| Polyoxyethylene sorbitol fatty acid ester (40E.O.) | 9 |
| Polyoxyethylene sorbitol fatty acid ester (20E.O.) | 3 |
| Perfume | trace |

What is claimed is:

1. A lipolysis acceleration method, which comprises orally administering or dermatologically applying an effective amount of a thistle-series or pepper-family plant or an extract thereof.

2. A method according to claim 1, wherein the thistle series plant is *Cephalonoplos segetnum* (Bieb.) Kitam or *Cirsium japonicum* DC.

3. A method according to claim 1, wherein the pepper family plant is *Piper nigrum* L or *Piper longum* L.

4. A method according to claim 1, wherein the dermatologic application is conducted by applying the thistle-series or pepper-family plant or the extract thereof to the skin; or by bathing in a bathwater containing the thistle-series or pepper-family plant or the extract thereof.

5. A dermatologic medicine composition comprising an effective amount of (a) a thistle-series plant or an extract thereof; and (b) a dermatological medicine ingredient, wherein the thistle-series plant is selected from the group consisting of Cephalonoplos, Carduns, Saussurea, Hemistepta, Synurus, Serratula, Atractylodes, Echinops, *Cirsium purpuratum, Cirsium pendulum, Cirsium ugoense, Cirsium grayanum, Cirsium kamtschaticum, Cirsium sieboldii, Cirsium lucens, Cirsium yezoense, Cirsium tenuisquamatum, Cirsium tashiori, Cirsium hidaense, Cirsium spinosum, Cirsium maritimum, Cirsium brevicaule, Cirsium boninense, Cirsium oligophyllum, Cirsium chokaiense, Cirsium borealinipponense, Cirsium okamotoi, Cirsium maruyamanum, Cirsium diabolicum, Cirsium magofukui, Cirsium lineare, Cirsium dipsacolepis, Cirsium kagomontanum, Cirsium suzukii, Cirsium gyojanum, Cirsium confertissimum, Cirsium bitchuense, Cirsium aidzuense, Cirsium buevgeri, Cirsium longepedunculatum, Cirsium heiianum, Cirsium suzukaense, Cirsium furusei, Cirsium eausum, Cirsium congestissimum, Cirsium spicatum, Cirsium tenue, Cirsium microspicatum, Cirsium inundatum, Cirsium norikurense, Cirsium amplexifolium, Cirsium matsumurae, Cirsium ganjuense, Cirsium babanum, Cirsium suffultum, Cirsium nipponicum, Cirsium yakushimense, Cirsium chikushiense* and *Cirsium hanamakiense*.

6. A dermatologic composition according to claim 5, wherein the thistle series plant is *Cephalonoplos segetnum* (Bieb.) Kitam.

7. A dermatologic composition according to claim 5 suitable for use in the acceleration of lipolysis.

8. A bath medicine composition comprising an effective amount of (a) a thistle-series plant or an extract thereof; and (b) a bath medicine ingredient.

9. A bath medicine composition according to claim 8, wherein the thistle series plant is *Cephalonoplos segetnum* (Bieb.) Kitam or *Cirsium japonicum* DC.

10. A bath medicine composition according to claim 8 suitable for use in the acceleration of lipolysis.

* * * * *

UNITED STATES PATENT AND TRADEMARK OFFICE
CERTIFICATE OF CORRECTION

PATENT NO. : 5,698,199
DATED : December 16, 1997
INVENTOR(S) : Shinobu MORI ET AL It is certified that error appears in the above-identified patent and that said Letters Patent is hereby corrected as shown below:

Column 16, line 35, "*Cirsium eausum*," should read --*Cirsium effusum*,--.

Signed and Sealed this

Third Day of March, 1998

*Attest:*

BRUCE LEHMAN

*Attesting Officer*   Commissioner of Patents and Trademarks